(12) United States Patent
Yamano et al.

(10) Patent No.: US 8,229,196 B2
(45) Date of Patent: Jul. 24, 2012

(54) METHOD OF DETECTING SPECIFIC POLYMER CRYSTAL

(75) Inventors: Akihito Yamano, Akishima (JP); Takahisa Sato, Akishima (JP); Hiroki Yoshida, Akishima (JP); Motohide Yoshimura, Kobe (JP); Kensaku Hamada, Himeji (JP)

(73) Assignees: Rigaku Corporation, Saitama (JP); Riken, Saitama (JP)

( * ) Notice: Subject to any disclaimer, the term of this patent is extended or adjusted under 35 U.S.C. 154(b) by 0 days.

(21) Appl. No.: 13/006,883

(22) Filed: Jan. 14, 2011

(65) Prior Publication Data

US 2011/0164795 A1 Jul. 7, 2011

Related U.S. Application Data

(63) Continuation-in-part of application No. 10/569,044, filed on Feb. 21, 2006, now Pat. No. 8,041,086.

(30) Foreign Application Priority Data

Aug. 18, 2003 (JP) .................................. 2003-207772

(51) Int. Cl.
*G06K 9/00* (2006.01)

(52) U.S. Cl. ......................... 382/128; 382/130; 382/131

(58) Field of Classification Search .................. 382/128, 382/130, 131; 378/44–51; 356/317, 318, 356/302, 326

See application file for complete search history.

(56) References Cited

U.S. PATENT DOCUMENTS

| | | | | |
|---|---|---|---|---|
| 3,864,571 | A | * | 2/1975 | Stillman et al. ................ 250/302 |
| 4,964,150 | A | * | 10/1990 | Van Der AA et al. ......... 378/197 |
| 6,117,232 | A | * | 9/2000 | Sanjoh ............................. 117/70 |
| 6,123,769 | A | * | 9/2000 | Sanjoh ........................... 117/206 |
| 7,227,983 | B1 | * | 6/2007 | Christian et al. .............. 382/141 |
| 7,342,995 | B2 | * | 3/2008 | Sato et al. ........................ 378/46 |
| 2002/0067800 | A1 | * | 6/2002 | Newman et al. ................ 378/73 |

* cited by examiner

*Primary Examiner* — Vikkram Bali
*Assistant Examiner* — Nancy Bitar
(74) *Attorney, Agent, or Firm* — Jordan and Hamburg LLP

(57) ABSTRACT

In a specific macromolecule crystal detecting method according to the present invention, ultraviolet light is irradiated to sample solution, and a fluorescent image emitted from a sample in the sample solution is detected to detect specific macromolecules in the sample solution. Furthermore, by detecting the outline of the sample from the visible light image of the sample contained in the sample solution, the crystal is discriminated from other materials on the basis of the outline. By integrating the detection results of the fluorescent image and the visible light image, the specific macromolecule crystal is detected from the sample solution.

3 Claims, 11 Drawing Sheets

Fig.5

| 3 | 2 | 1 |
|---|---|---|
| 4 | NOTED PIXEL (x, y) | 8 |
| 5 | 6 | 7 |

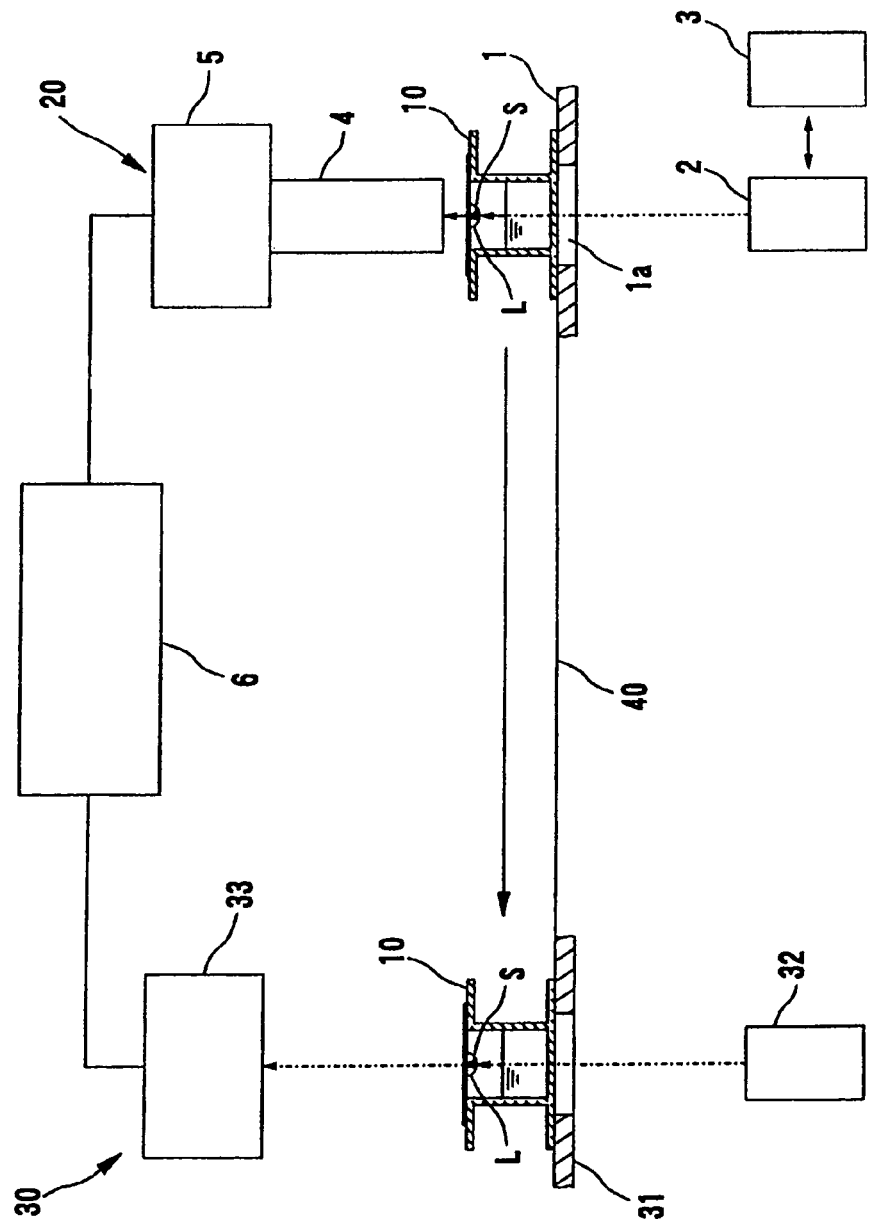

METHOD OF DETECTING SPECIFIC POLYMER CRYSTAL

The present application is a Continuation-In-Part of U.S. patent application Ser. No. 10/569,044, filed Feb. 21, 2006, now U.S. Pat. No. 8,041,086, the contents of which are incorporated herein by reference.

BACKGROUND OF THE INVENTION

The present invention relates to a detection method of detecting a specific polymer crystal, namely a specific macromolecule crystal in sample solution.

Worldwide attention has been paid to the structural analysis of protein crystals in connection with the development in the genome plane since a double helix structure of DNA was discovered. A method using NMR (Nuclear Magnetic Resonance apparatus) a method using an electron microscope, a method using the X-ray diffraction phenomenon, etc. have been developed for the structure analysis of protein crystals, and particularly the X-ray crystal structure analysis using the X-ray diffraction phenomenon has been rapidly advanced in connection with the developments of a two-dimensional X-ray detector such as an imaging plate or the like, analyzing software for two-dimensional data, etc.

In the protein crystal structure analysis using the X-ray diffraction phenomenon, it has been hitherto general that a protein crystal grain achieved by crystallizing protein in solution is first poured into a narrow tube called as a capillary together with the solution, and the capillary concerned is mounted in an X-ray diffraction device.

In order to carry out the X-ray structural analysis of protection crystals by using the X-ray diffraction deice as described above, a protein crystal as a target must be accurately positioned to an X-ray irradiating position. Therefore, after a sample solution poured capillary is mounted in the X-ray diffraction device, the protein crystal in the capillary is visually observed by using a microscope, and it is manually positioned to the X-ray irradiating position.

The search of the protein crystal through the visual observation as described above and the positioning work are cumbersome and take much time. In addition, these works must be carried out every time one measuring operation is finished, and thus this method is unsuitable to rapidly measure/evaluate many samples automatically.

The number of proteins constituting a human body extends to 50,000 to 100,000 kinds of proteins, and it has been urgently required in the recent structural biology to clarify many protein structures in a short time.

The present invention has been implemented in view of the foregoing situation, and has an object to provide a specific macromolecule crystal detecting method that can easily search a specific macromolecule crystal sample from sample solution and contribute to the quick processing of measuring/evaluating specific macromolecule crystals.

SUMMARY OF THE INVENTION

In order to attain the above object, a specific macromolecule crystal detecting method according to the present invention is characterized in that a sample in a sample container is identified as a specific macromolecule under the condition that the sample in the solution generates fluorescence when ultraviolet light is irradiated to the sample solution, and it is judged on the basis of a visible light image of the sample whether the sample is a crystal or not.

Furthermore, a specific macromolecule crystal detecting method comprises:

a specific macromolecule detecting step of irradiating ultraviolet light to sample solution and detecting a fluorescent image emitted from a sample in the sample solution; and a crystal detecting step of detecting the outline of the sample from the visible light image of the sample contained in the sample solution, wherein a sample for which a fluorescent image is detected in the specific macromolecule detecting step and an outline indicating a crystal is detected in the crystal detecting step is identified as a specific macromolecule crystal.

Most of polymer crystals, particularly biological polymer generates fluorescence when ultraviolet light is irradiated thereto. In this specification, the polymer crystal having a characteristic that it generates fluorescence when ultraviolet light is irradiated to the polymer crystal will be referred to as "specific macromolecule crystal". For example, the protein crystals correspond to the specific macromolecule crystals.

According to the specific macromolecule crystal detecting method of the present invention, paying attention the characteristic of the specific macromolecule crystal as described above, ultraviolet light is irradiated to sample solution and a fluorescent image emitted from a sample in the sample solution is detected, thereby detecting specific macromolecule in the sample solution.

However, there is a case where it is unidentifiable on the basis of only the fluorescent image whether the detected specific macromolecule forms a crystal or not. For example, when aggregation of specific macromolecule exists in sample solution, the aggregation concerned generates fluorescence, and thus a fluorescent image of the crystal and a fluorescent image of the aggregation are detected with being mixed with each other.

Therefore, according to the specific macromolecule crystal detecting method of the present invention, the outline of the sample is detected on the basis of a visible light image of the sample contained in the sample solution to discriminate the crystal from materials other than the crystal on the basis of the outline, and the "crystal" of "specific macromolecule" is detected from the sample solution in cooperation with the detection result of the fluorescent image.

Furthermore, the specific macromolecule crystal according to the present invention further comprises a step of recognizing the position of the sample identified as a specific macromolecule crystal in addition to the above construction.

Furthermore, the crystal detecting step may comprise:

an image input step for achieving the visible light image of the sample contained in the sample solution as image data;

an image processing step for binarizing the image data of the visible light image thus achieved;

an edge detecting step of detecting pixels corresponding to an edge of the sample contained in the sample solution from the binarized image data;

a contour line detecting step of searching continuity of the pixels corresponding to the edge of the detected sample and detecting a closed contour line of the sample; and a gravity center detecting step of recognizing an internal area of the closed contour line and detecting the position of the center of gravity of the internal area.

A sample having a closed contour line recognized in the crystal detecting step is evaluated as a crystal having a constant area, and a sample whose contour line is not closed is evaluated as a non-crystallized sample such as aggregation or the like. Therefore, attention is paid to only the sample having the closed contour line, and the gravity center position of the sample concerned is detected. It can be judged by integrating the identification result of the specific macromolecule detecting step whether the sample is a specific macromolecule crystal or not.

The specific macromolecule crystal detecting method according to the present invention can perform automatic processing based on computer processing. Accordingly, it can be utilized by automating the measurement/evaluation of specific macromolecule crystal samples, and it is expected to contribute to the rapid processing of the measurement/evaluation.

BRIEF DESCRIPTION OF THE DRAWINGS

FIG. 5 is a diagram showing the edge detecting processing of step S11 shown in FIG. 4.

FIG. 6 is a diagram showing the scheme of a protein crystal evaluating device in which the specific macromolecule detecting device of FIG. 1 is installed.

DETAILED DESCRIPTION OF THE INVENTION

Preferred embodiments according to the present invention will be described with reference to the drawings. In the following embodiments, the description will be made on the assumption that a protein crystal is set as a detection target (a specific macromolecule crystal).

Figure 1:
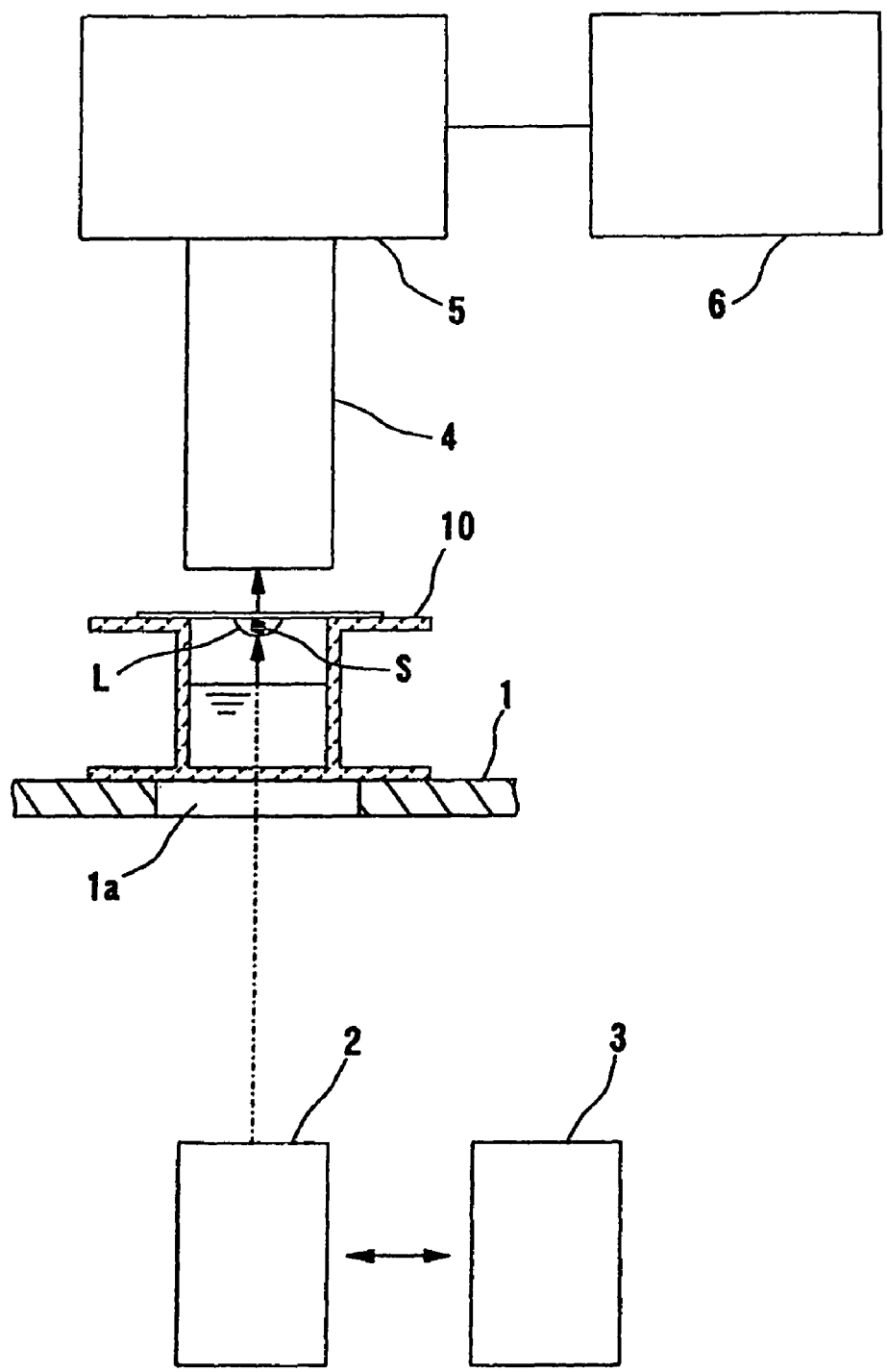
FIG. 1 is a diagram showing the scheme of a protein crystal detecting device suitable to execute the method of the present invention.

FIG. 1 is a diagram showing the scheme of a protein crystal detecting device suitable to execute the method of the present invention.

The protein crystal detecting device shown in FIG. 1 is equipped with a visible light irradiating unit 2 and a ultraviolet light irradiating unit 3 at the lower side of a sample table 1. The visible light irradiating unit 2 and the ultraviolet light irradiating unit 3 are light sources for irradiating visible light or ultraviolet light to sample solution L in a sample container 10 disposed on the sample table 1.

The visible light irradiating unit 2 and the ultraviolet light irradiating unit 3 are laterally slid so that any one of them is disposed so as to confront the sample container 10 on the sample table 1 through a through hole 1a. If a reflection mirror is disposed at the midpoint between the sample container 10 and each of the visible light irradiating unit 2 and the ultraviolet light irradiating unit 3 so that visible light emitted from the visible light irradiating unit 2 or ultraviolet light emitted from the ultraviolet light irradiating unit 3 is led to the sample container 10, it is unnecessary each of the irradiating units 2, 3 is disposed so as to confront the sample container 10.

The sample table 1 is provided with a through hole 1a through which visible light irradiated from the visible light irradiating unit 2 and ultraviolet light irradiating from the ultraviolet light irradiating unit 3 are transmitted, and the sample container 10 is mounted on the through hole.

Figure 2A:
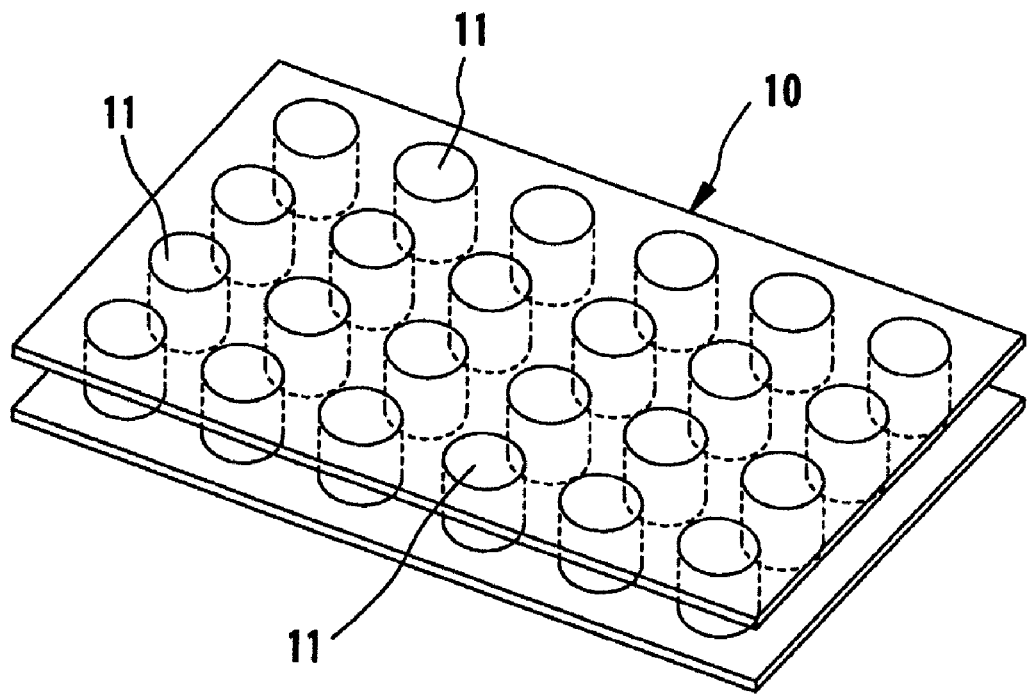
FIG. 2A is a perspective view showing a construction of a sample container.
Figure 2B:
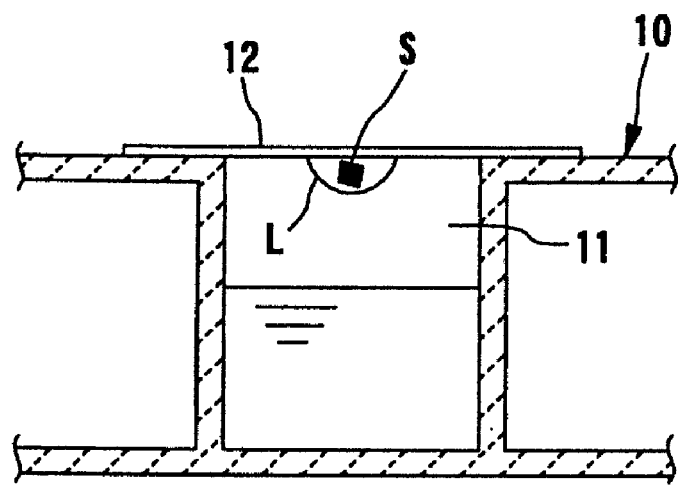
FIG. 2B is a partially enlarged front cross-sectional view showing the sample container.

It is preferable that a crystallization plate formed of material such as polyimide or the like through which ultraviolet light, visible light and X-ray are transmitted is used for the sample container 10. As shown in FIG. 2A, many recess portions 11 are formed on the sample container 10 using the crystallization plate, and protein crystals can be generated in the recess portions 11. Various methods containing a vapor diffusion method are known as a method of generating a protein crystal by using a crystallization plate. FIG. 2B is a schematic diagram showing a state where a protein crystal S is generated by the vapor diffusion method, and a protein crystal S is generated in a drop of sample solution L placed on the lower surface of a cover plate 12. Protein crystals are separately generated in the many recess portions formed on the sample container while the generation condition is varied, or different kinds of protein crystals can be separately generated therein.

Returning to FIG. 1, a microscope 4 and a two-dimensional image pickup unit 5 are disposed above the sample table 1. The microscope 4 enlarges an image achieved when ultraviolet light or visible light is irradiated to the sample solution L in the sample container 10 and then transmitted through the sample solution L, and leads the enlarged image to the two-dimensional image pickup unit 5. The microscope 4 may be designed so that the protein crystal S in the sample solution L can be searched by varying the focal position in the vertical direction.

For example, CCD may be used as the two-dimensional image pickup unit 5. The two-dimensional image pickup unit 5 converts the enlarged image incident through the microscope 4 to an electrical signal (image data), and outputs the electrical signal to the central processing unit (CPU) 6. The central processing unit 6 processes the image data input from the two-dimensional image pickup unit 5 to detect the protein crystal S in the sample solution L and also recognize the position thereof.

Next, a protein crystal detecting method using the above device will be described.

Figure 3:
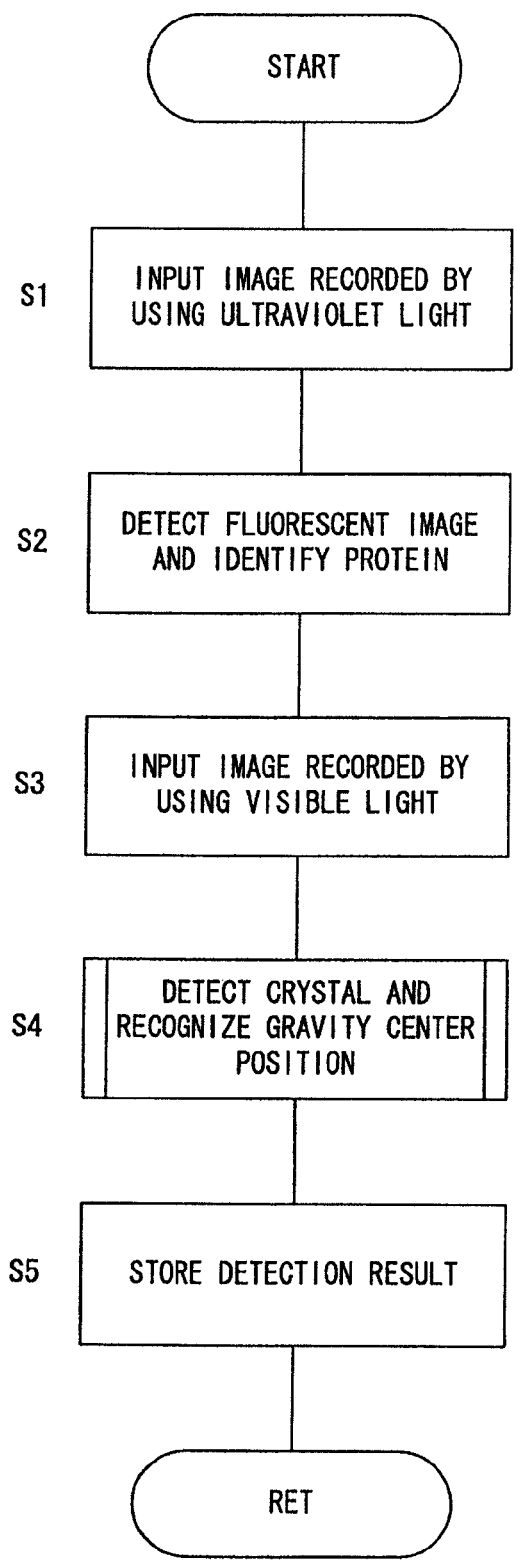
FIG. 3 is a flowchart showing a protein crystal detecting method executed by a central processing unit.
Figure 4:
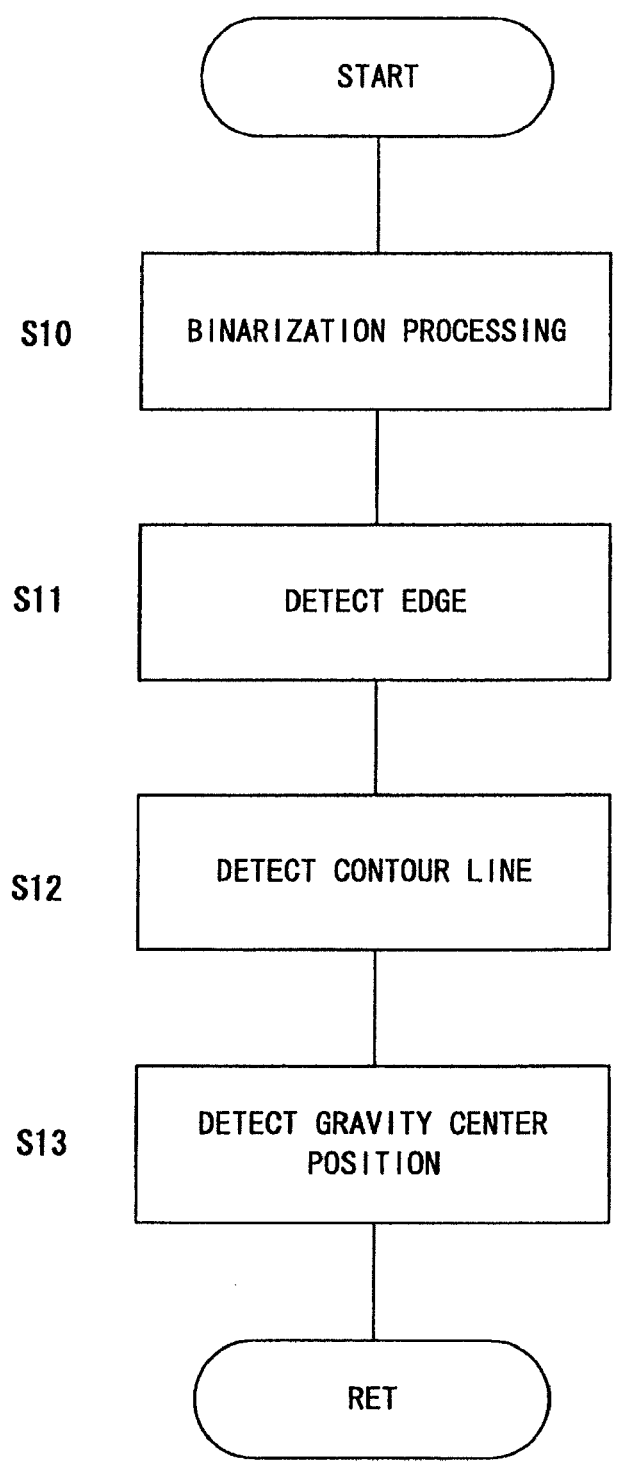
FIG. 4 is a flowchart showing a subroutine according to step S4 of FIG. 3.

FIGS. 3 and 4 are flowcharts showing the protein crystal detecting method executed by the central processing unit.

First, the sample container 10 in which the protein crystal S is generated in the sample solution L is disposed on the through hole 1a of the sample table 1. Subsequently, a light source is set to the ultraviolet irradiating unit 3, and ultraviolet light emitted from the ultraviolet light irradiating unit 3 is irradiated to the sample solution L in the sample container 10.

At this time, an image achieved when the light is transmitted through the sample solution L in the sample container 10 is enlarged by the microscope 4 and then incident to the two-dimensional image pickup unit 5. The central processing unit 6 receives the image data transmitted from the two-dimensional image pickup unit 5 (step S1), and detects the fluorescent image from the image data (step S2). That is, the protein crystal S generated in the sample solution L generates fluorescence when ultraviolet light is irradiated thereto, and thus the fluorescent image thereof is incident to the two-dimensional image pickup unit 5. Therefore, the central processing unit 6 analyzes the image data input from the two-dimensional image pickup unit 5 to detect the fluorescent image and grasp the position of the fluorescent image, that is, the protein. The position of the protein thus grasped corresponds to a position on the horizontal plane (XY coordinate), and the position in the height direction (z coordinate) is grasped on the basis of the focal position of the microscope 4.

Subsequently, the light source is switched from the ultraviolet light irradiating unit 3 to the visible light irradiating unit 2, and irradiates the visible light emitted from the visible light irradiating unit 2 to the sample solution L in the sample container 10. At this time, a visible light image achieved through the sample solution L in the sample container 10 is enlarged by the microscope 4 and then incident to the two-dimensional image pickup unit 5. The central processing unit 6 receives the image data transmitted from the two-dimensional image pickup unit 5 (step S3), and processes the image data to detect a crystal in the sample solution L and also recognize the position of the gravity center of the crystal (step S4).

The step S4 (crystal detecting step) is processed along a subroutine shown in FIG. 4. That is, the image data input from the two-dimensional image pickup unit 5 is subjected to binarization processing by using a predetermined threshold value as a reference, and converts each pixel on the xy coordinate to binary data of "1" or "0" (step S10).

Figure 5:
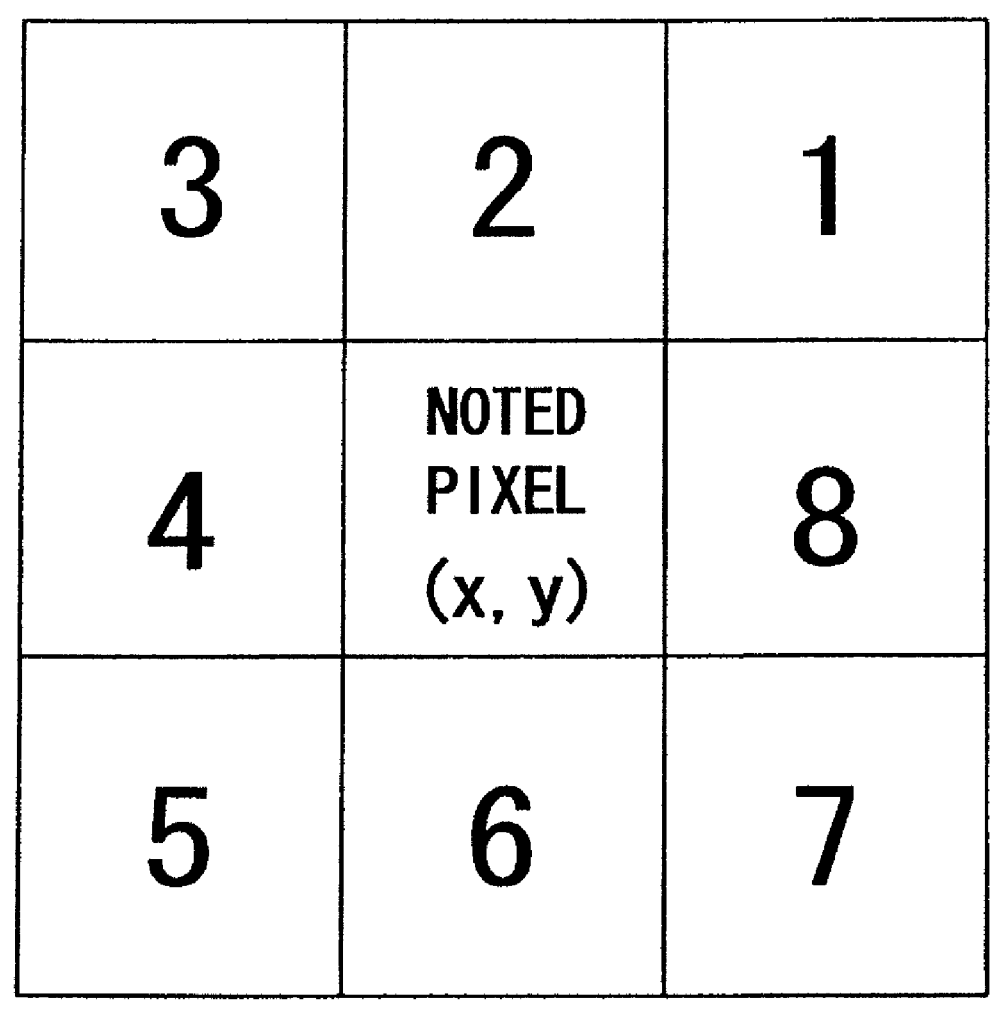

Subsequently, the pixels corresponding to the edge of a sample existing in the sample solution are detected on the basis of the binarized image data (step S11). In this case, for example it is judged whether a noted pixel as a identification target is black (data "1") as shown in FIG. 5, and if it is black, it is identified for the surrounding pixels (pixels 1 to 8) of the noted pixel concerned whether each of them is black (data "1") or white (data "0").

If all the surrounding pixels (pixels 1 to 8) are white (data "0"), it is concluded that the noted pixel is an isolated point. If all the surrounding pixels (pixels 1 to 8) are black (data "1"), it is concluded that the noted pixel concerned is an internal point of an image. As described above, all the pixels corresponding to isolated points and internal points are excluded, and a noted pixel for which some of surrounding pixels (pixels 1 to 8) of the noted pixel concerned are white (data "0") is recognized as an edge of the sample, and the xy coordinate of the noted pixel concerned is stored.

The above processing is executed on all the pixels on the xy coordinate system, and all the pixels corresponding to the edge of the sample are extracted.

Subsequently, the pixels corresponding to the edge of the sample thus extracted are noted, and the neighboring pixels thereof are linked to one another to detect the contour line of the sample (step S12). If the start and end points of the contour line are coincident with each other, the contour line is identified as a closed contour line. The sample having the closed contour line is identified as a crystal having a constant area. On the other hand, the sample whose contour line is not closed is excluded as a non-crystallized material such as aggregation or the like.

Subsequently, the internal area of the sample having the closed contour line (that is, crystal) is recognized, and the gravity center position of the internal area is calculated by a well-known calculation method (step S13).

As a method of calculating the gravity center position of a planar image, for example, the moment quantity of a linked figure S recognized as a crystal is calculated, and the gravity center position is calculated from this moment quantity. That is, when the weight of each pixel of the linked figure S is equally set to 1, the moment M(m, n) is defined by the following equations.

$$M(m, n) = \sum_{(x,y) \in S} (x^m \times y^n)$$

M(0, 0) represents the area of the linked figure S
M(1, 0) represents the moment with respect to the x-axis
M(0, 1) represents the moment with respect to the y-axis The gravity center coordinate (p, q) can be calculated by using the above moment quantity according to the following equations:

P=M(1,0)/M(0,0)

Q=M(0,1)/M(0,0)

After the gravity center position of the crystal thus detected is calculated, the central processing unit 6 returns to the main routine shown in FIG. 3 again, and superposes the position of the protein detected on the basis of the fluorescent image with the position of the crystal detected on the basis of the visible light image to recognize the protein crystal S. The gravity center position achieved n step S13 of FIG. 4 for the protein crystal S is stored (step S5). As described above, the gravity center position of the protein crystal S existing in the sample container 10 can be automatically detected.

FIG. 6 is a diagram showing the scheme of a protein crystal evaluating device in which a specific macromolecule detecting device is installed.

The specific macromolecule detecting device 20 can constitute a device for automatically evaluating a protein crystal in combination with an X-ray diffraction apparatus 30. That is, the sample table 1 of the specific macromolecule detecting device 20 and a sample table 31 of the X-ray diffraction apparatus 30 are connected to each other by moving means 40 such as an X-Y table or the like, and the sample container 10 is automatically fed from the specific macromolecule detecting device 20 to the X-ray diffraction apparatus 30, whereby evaluation of the protein crystal S can be automatically carried out by the X-ray diffraction apparatus 30.

As well known, the X-ray diffraction apparatus 30 is equipped with an X-ray source 32 and an X-ray detector 33, and when X-ray emitted from the X-ray source 32 is irradiated to the protein crystal S, diffracted X-ray emitted at a predetermined diffraction angle is detected by the X-ray detector 33. The diffraction angle at which the diffracted X-ray is emitted is determined by the crystal structure of material, and thus the structure of a protein crystal can be evaluated on the basis of the diffraction angle.

Here, in order to execute the evaluation of the protein crystal by the X-ray diffraction apparatus 30, it is necessary to accurately position the protein crystal to the X-ray irradiation position. Therefore, first, the gravity center position of the protein crystal S existing in the sample container 10 is detected by using the specific macromolecule detecting device 20, and the moving means 40 is controlled to feed the sample container 10 so that the gravity center position concerned is positioned to the X-ray irradiating position of the X-ray diffraction apparatus 30.

By using the protein crystal evaluating device thus constructed, a protein crystal generated in each recess portion 11 of the crystallization plate as shown in FIG. 2 can be automatically measured/evaluated, and the working can be facilitated and the speed-up of the measurement/evaluation can be implemented.

EXAMPLES

Figure 7A:
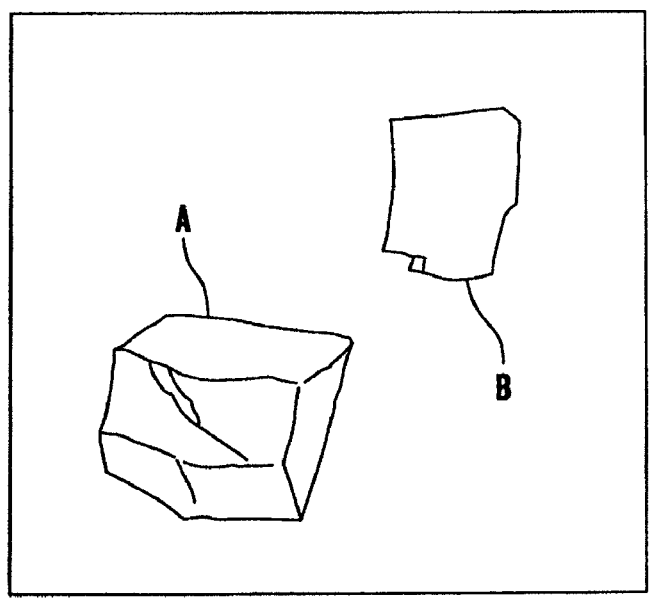
FIG. 7A, 7B are sketches of microscope images achieved by observing sample solution in which a protein crystal and a crystal of material generating self-fluorescence are mixed.
Figure 7B:
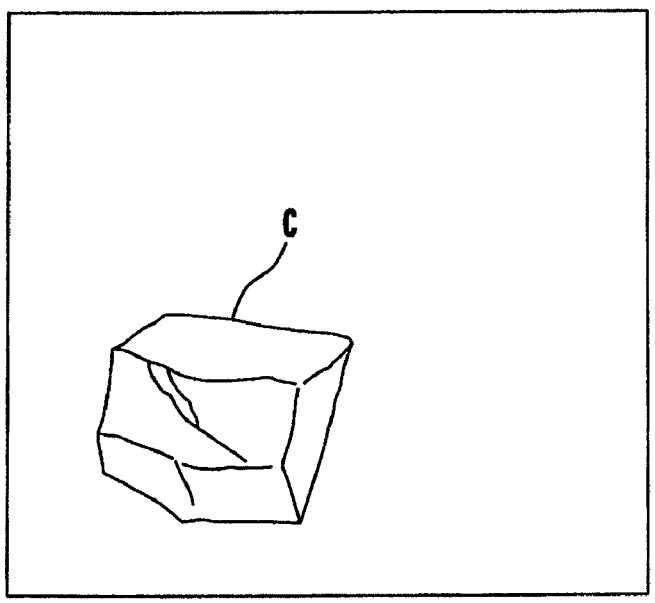

FIGS. 7A and 7B are sketches of microscope images achieved by observing sample solution in which a protein crystal and a crystal of material generating no self-fluorescence were mixed, wherein FIG. 7A shows a visible light image achieved by irradiating visible light to the sample solution, and FIG. 7B shows a fluorescent image achieved by irradiating ultraviolet light to the sample solution.

As shown in FIG. 7A, when visible light was irradiated to the sample solution, a visible light image A of the protein crystal and a visible light image B of another crystal were observed. It is unidentifiable on the basis of the above image which one of the visible light images corresponds to the protein crystal.

However, as shown in FIG. 7B, when ultraviolet light was irradiated to the sample solution, only a fluorescent image C of the protein crystal was observed, and the other crystal was not detected. Accordingly, by superposing the visible light image A and the fluorescent image C on each other, the position of the protein crystal could be recognized.

Figure 8A:
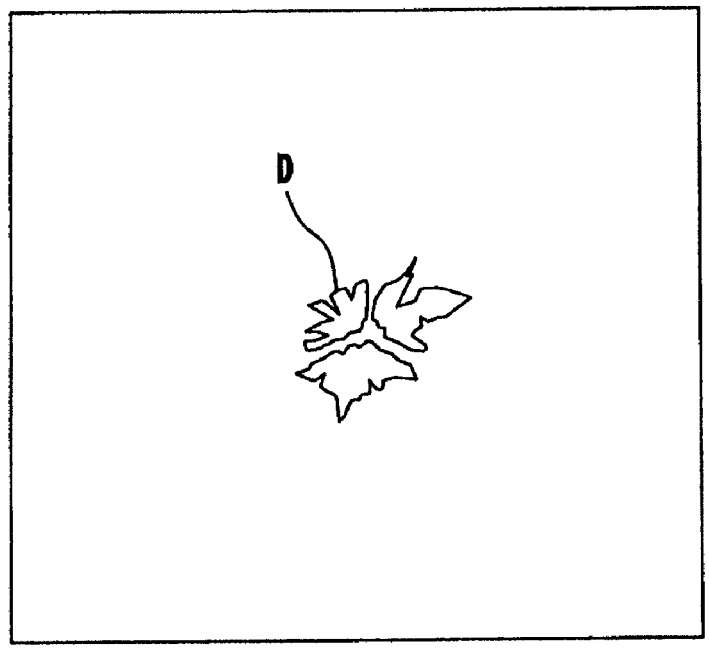
FIG. 8A, 8B are sketches of microscope images achieved by observing sample solution in which aggregation of protein is contained.
Figure 8B:
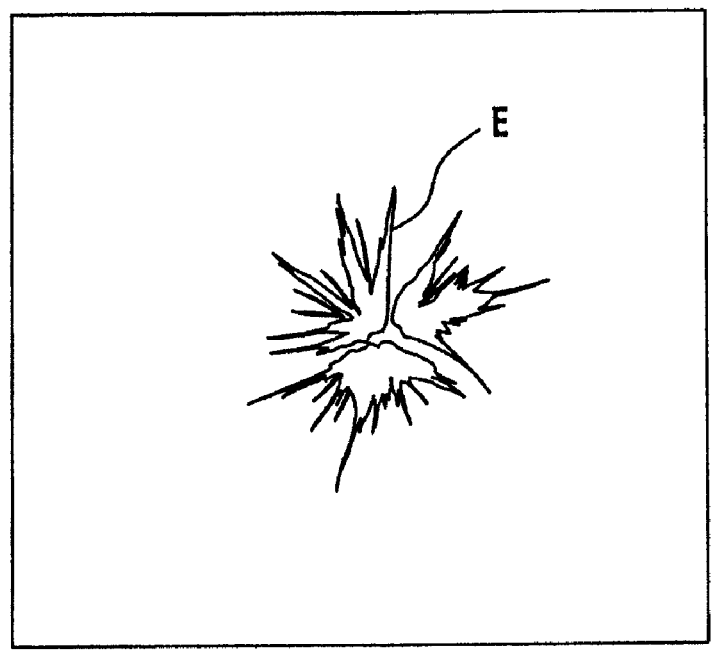

FIGS. 8A, 8B are sketches of microscope images achieved by observing the sample solution in which aggregation of protein was contained, wherein FIG. 8A is a fluorescent image achieved by irradiating ultraviolet light to the sample solution, and FIG. 8B is a visible light image achieved by irradiating visible light to the sample solution.

As shown in FIG. 8A, when ultraviolet light was irradiated to the sample solution, a fluorescent image D emitted from the aggregation of protein was observed. It is unidentifiable on the basis of the above fluorescent image D whether it is the aggregation of the protein or the crystal of the protein.

However, as shown in FIG. 8B, when visible light is irradiated to the sample solution, in the case of aggregation of protein, no clear ridge line of a crystal is observed, and it is discontinuous or have a needle-like outline in many cases. Accordingly, on the basis of this fact, it can be judged whether the observation target is aggregation of protein or the like.

Figure 9A:
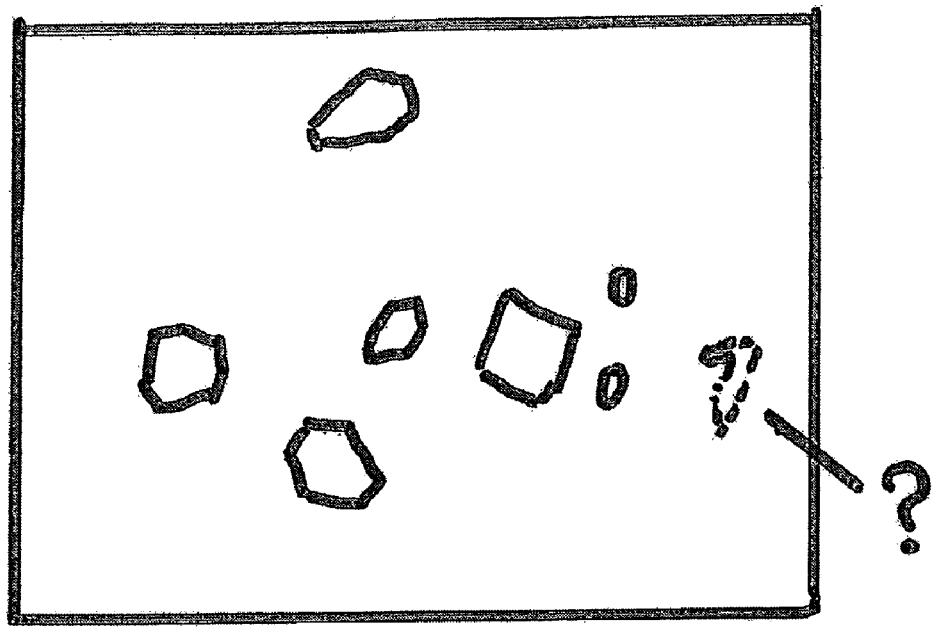
FIG. 9A, 9B are sketches of microscope images of observations of a sample with visible light.
Figure 9B:
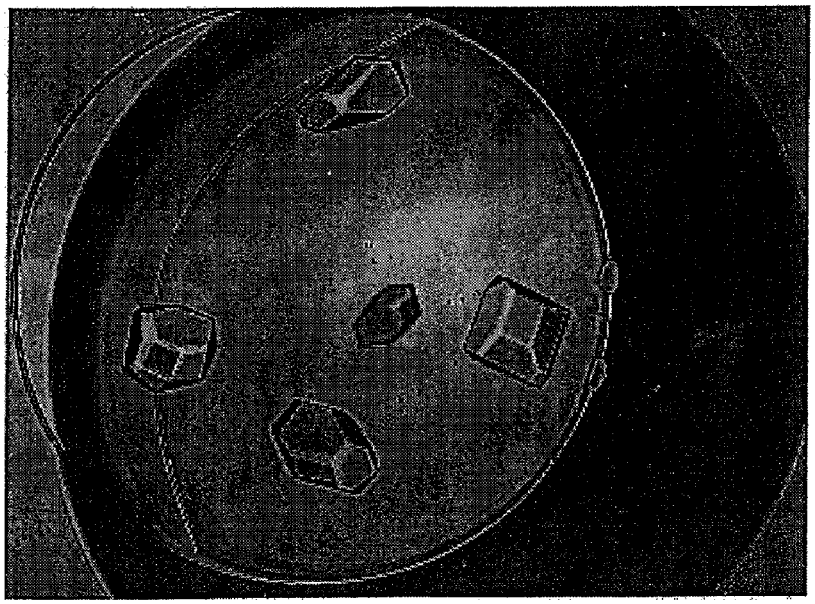
Figure 10A:
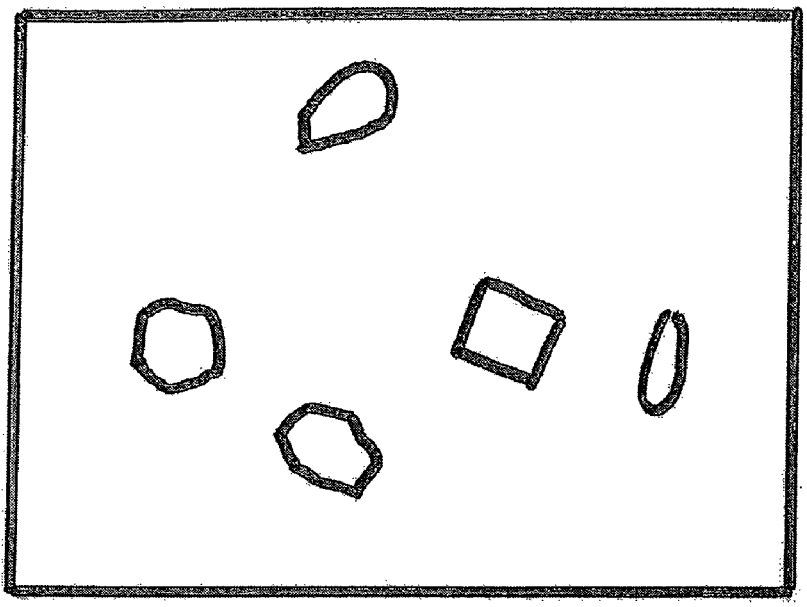
FIG. 10A, 10B are sketches of microscope images of observations of a sample with ultraviolet light.
Figure 10B:
Figure 11:
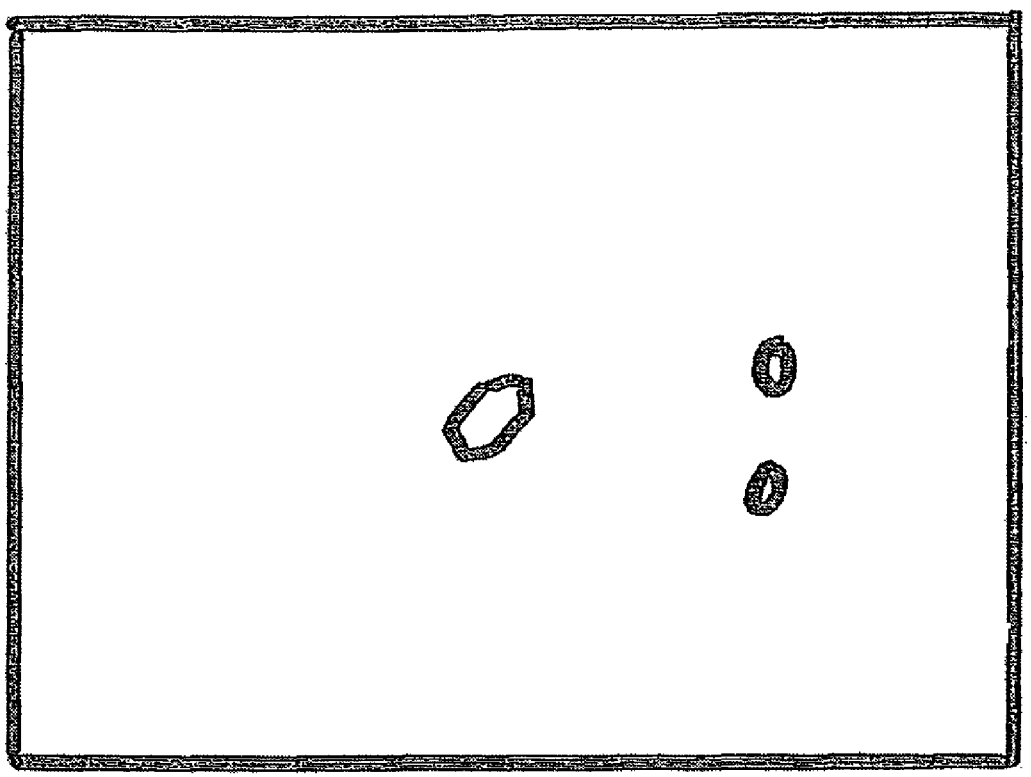
FIG. 11 is a sketch of a microscope image identifying the only those crystals shown in FIGS. 9A and 9B that are observable in visible light.

FIGS. 9A and 9B show the observation of crystals in a sample illuminated with visible light. A specific crystal deposited on the wall of the well, in the right side of FIG. 9B, is not easily observed, as reflected in its depiction in FIG. 9A, where it is shown with a dotted outline. However, because crystals of specific macromolecules fluoresce when irradiated with UV light, such crystals that are otherwise hard-to-see become clearly visible when irradiated with UV light. Specifically, FIGS. 10A and 10B show the crystals of FIGS. 9A and 9B being irradiated with UV light. In comparison to what is shown in FIGS. 9A and 10B, the UV light source renders only those crystals visible that irradiate UV light, which are the crystals of specific macromolecules. Also, the crystal on the wall of the well, which was not easily visible with visible light, is now readily visible. Also, FIG. 11 is a sketch of a microscope image identifying only those crystals shown in FIGS. 9A and 9B that are observable in visible light.

As described above, by integrating the fluorescent image achieved when ultraviolet light is irradiated to sample solution and the visible light image achieved when visible light is irradiated to the sample solution, the position of the protein crystal can be recognized with excluding crystals other than the protein crystal and aggregation of protein.

In the above embodiments and examples, the description has been made by setting the protein crystal as a detection target, however, the target of the method of the present invention is not limited to the protein crystal. Various kinds of specific macromolecule crystals having the characteristic that they generates fluorescence when ultraviolet light is irradiated thereto can be set as detection targets.

As described above, according to the present invention, the specific macromolecule crystal can be easily searched by integrating the fluorescent image achieved when ultraviolet light is irradiated to sample solution and a visible light image achieved when visible light is irradiated to the sample solution.

The invention claimed is:

1. A method for differentiating between specific macromolecule crystals irradiating UV light and crystals that do not irradiate UV light which are contained in a crystal-containing sample in solution, comprising the steps of
   detecting specific macromolecule crystals that irradiate UV light by irradiating the crystal-containing sample in solution with UV light and detecting a fluorescent image emitted from the specific macromolecule crystals that irradiate UV light;
   determining the location of the specific macromolecule crystals that irradiate UV light based upon the detecting of the fluorescent image emitted from the specific macromolecule crystals that irradiate UV light;
   detecting crystals that do not irradiate UV light by irradiating the crystal-containing sample in solution with visible light and detecting a visible light image emitted from crystals that are observable in visible light;
   determining the location of the crystals that are observable in visible light based upon the detecting of the visible light image emitted from the crystals that are observable in visible light;
   comparing the location of the specific macromolecule crystals that irradiate UV light and the location of the crystals that are observable in visible light;
   differentiating between the specific macromolecule crystals irradiating UV light and crystals that do not irradiate UV light based upon information collected in the comparing step.

2. A method for differentiating between specific macromolecule crystals irradiating UV light and crystals that do not irradiate UV light which are contained in a crystals-containing sample in solution, comprising the steps of
   a specific macromolecule detecting step of irradiating a sample solution with ultraviolet light and detecting a fluorescent image emitted from a sample in the sample solution;
   a crystals detecting step of detecting the outline of the sample from the visible light image of the sample contained in the sample solution, wherein a sample for which a fluorescent image is detected in the specific macromolecule detecting step and an outline indicating crystals is detected in the crystals detecting step is identified as specific macromolecule crystals;
   determining the location of the sample identified as specific macromolecular crystals;
   detecting crystals that do not irradiate UV light by irradiating the sample in solution with visible light and detecting a visible light image emitted from crystals that are observable in visible light;
   determining the location of the crystals that are observable in visible light based upon the detecting of the visible light image emitted from the crystals that are observable in visible light;
   comparing the location of the specific macromolecule crystals that irradiate UV light and the location of the crystals that are observable in visible light;
   differentiating between the specific macromolecule crystals irradiating UV light and crystals that do not irradiate UV light based upon information collected in the comparing step.

3. The specific macromolecule crystals detecting method according to claim 2, wherein the specific macromolecule crystals are protein crystals.

* * * * *

UNITED STATES PATENT AND TRADEMARK OFFICE
CERTIFICATE OF CORRECTION

PATENT NO. : 8,229,196 B2
APPLICATION NO. : 13/006883
DATED : July 24, 2012
INVENTOR(S) : Akihito Yamano et al.

It is certified that error appears in the above-identified patent and that said Letters Patent is hereby corrected as shown below:

Title Page, item (73) please change

(73) Assignees: from "Rigaku Corporation, Saitama (JP)"
to --Rigaku Corporation, Tokyo (JP)--

Signed and Sealed this
Twenty-second Day of January, 2013

David J. Kappos
*Director of the United States Patent and Trademark Office*